United States Patent [19]

Roiret et al.

[11] 4,311,388
[45] Jan. 19, 1982

[54] VISIBILITY MEASURING DEVICE

[75] Inventors: Michel C. Roiret, Massy; Aime M. Salles, Courbevoie, both of France

[73] Assignee: Societe Nationale d'Etude et de Construction de Moteurs d'Aviation, Paris, France

[21] Appl. No.: 88,156

[22] Filed: Oct. 25, 1979

[30] Foreign Application Priority Data

Oct. 30, 1978 [FR] France .................. 78 30728

[51] Int. Cl.³ .......................................... G01N 21/00
[52] U.S. Cl. ..................................... 356/341; 356/343
[58] Field of Search ................ 356/338, 339, 341, 343

[56] References Cited
U.S. PATENT DOCUMENTS 3,185,975  5/1965  Kompelien ............... 356/338 X
3,563,661  2/1971  Charlson et al. .......... 356/339

FOREIGN PATENT DOCUMENTS 2173148 10/1973 France .
2214897  8/1974 France .

Primary Examiner—John K. Corbin
Assistant Examiner—Matthew W. Koren
Attorney, Agent, or Firm—Oblon, Fisher, Spivak, McClelland & Maier

[57] ABSTRACT

A device for measuring the visibility, or diffusion coefficient, of atmosphere air, including a light source for directing light onto a volume of air and a receiver capable of measuring the flow of light diffused by the volume of air. The source is surrounded by ambient air and furnishes a beam diverging in essentially all directions except within at least one dark cone. A receiver opening is directed toward the source, but is located in the dark cone so as to receive only diffused light. The apparatus is for use in meteorological installations, notably in airports.

10 Claims, 4 Drawing Figures

VISIBILITY MEASURING DEVICE

BACKGROUND OF THE INVENTION

1. Field of the Invention

The present invention concerns a visibility measuring device of the type comprising a source directing an incident beam of modulated light onto a volume of ambient air and a receiver comprising a detector measuring the flow of modulated light diffused by the volume of air.

2. Description of the Prior Art

In a known device of this type (French utility patent No. 2214897), diffused light is measured only in the direction opposite that of the incident beam. It has been observed that the measurement of the light diffused by retrodiffusion does not possess a satisfactory correlation with the total diffusion coefficient of the volume of air. The information yielded by this type of known apparatus is thus marred by considerable error as a function of the nature of the aerosol. The applicants' studies show a non-compensatable systematic error (which is a function of the nature of the aerosol contained in the air) on the diffusion coefficient of between −50% and +100%.

Furthermore, the visibility measuring accuracy of this known apparatus further suffers since the measured accuracy based on the retrodiffusion principle is dependent on the physical condition of glass windows separating the beam source and the detector, e.g. stains on the glass windows adversely effect the accuracy of the visibility measurement.

In conclusion, while the process for measuring visibility by retrodiffusion is technically the simplest, it is also the least satisfactory in practice.

SUMMARY OF THE INVENTION

Accordingly, one object of this invention is to provide a novel visibility measuring device which eliminates the above-described drawbacks of the prior art devices.

It is the further object of this invention to provide a device capable of measuring the average diffusion within an angular range running essentially from 0° to 180° with respect to the directon of primary radiation.

These and other objects are achieved according to the invention by providing a novel visibility measuring device in which the source is surrounded by ambient air exhibiting a diffusion coefficient to be measured and is of the type which provides a beam diverging in essentially all directions except within at least one dark cone. The receiver is located in an enclosed housing in which is disposed a first detector separated from the source by a detector entry window. The detector entry window is directed toward the source and is located in the dark cone, in consideration of which the first detector, even if it presents a small entry opening, may receive light diffused by the volume of ambient air along diffusion angles distributed within a large area from some few degrees up to more than 120°.

Advantageously, the detector entry window has a rotational shape centered on the axis of the dark cone of the source, in consideration of which the entry window may have a small surface, so as to avoid reception of interference light by the first detector, without significantly reducing the quantity of diffused light received by the first detector.

Advantageously, the detector entry window is substantially annular in shape.

Advantageously, the half-angle at the peak of the dark cone is between 5° and 40°.

Advantageously, the receiver further includes a second detector intended for measuring the direct flow of light provided by the source. The second detector receives directly a portion of the beam emitted by the source, with the entry window of the second detector being substantially annular and surrounding that of the first detector.

Advantageously, the entry window of the first and/or second detector(s) is, or are, each governed by the opening of a diaphragm.

Advantageously, the two detectors are disposed within a sole closed, thermally insulated housing having a transparent surface facing the source.

Advantageously, the source is compact in shape.

The applicants have observed that if the angular field is limited, e.g. to between 10° and 120°, the systematic error as a function of the nature of the diffusing aerosol in the ambient air is a maximum of 11% of the measurement of the total diffusion coefficient. This value results particularly from measurements performed in natural aerosol.

Low analysis volume for such a device may be compensated by a temporal integration of the measurement over several minutes. This precaution in effect enables smoothing out of small-scale diffusion variations which lack importance. The reading delivered by such an apparatus therefore gives, because of the volume of air analyzed over the integration period, a horizontal visibility distance of satisfactory accuracy, even in the case of great visibility.

The good precision provided by such a method of measurement, the possibility of constructing such an apparatus in compact form and thus limiting problems of infrastructure, and the possibility of gaining independence from glass stains through addition of a simple complementary device render the device of the invention particularly useful.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
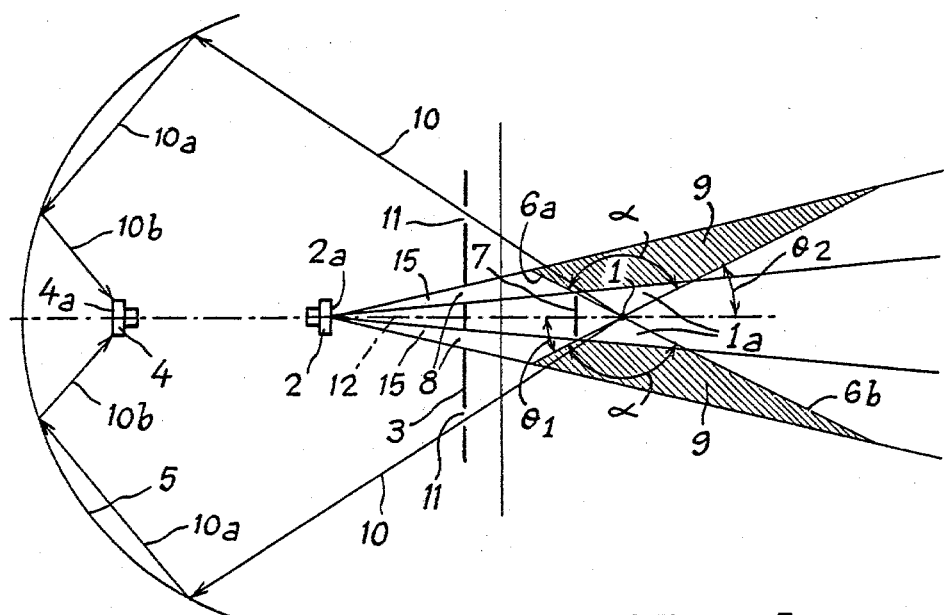
FIG. 1 is a schematic diagram showing the principle of the device according to one embodiment of the invention.

Referring now to the drawings, wherein like reference numerals designate identical or corresponding parts throughout the several views, and more particularly to FIG. 1 thereof, the device of the invention includes a source of modulated light 1 fed by electric current, a first light detector 2, the sensitive surface 2a of which is directed towards source 1, a diaphragm 3 placed between source 1 and detector 2, a second light detector 4 and a rotationally concave mirror 5, the concave reflecting surface of which is directed toward source 1 and detector 4.

Source 1 is of the type which emits a beam of light 1a diverging in all directions, except within two coaxial dark cones having opposite peaks 6a and 6b. Detector 2 is placed within dark cone 6a. A mask, or screen, is disposed between source 1 and detector 2 within dark cone 6a. The mask 7 prevents the rays of light diffracted by elements of source 1 itself from reaching detector 2. The latter thus does not receive any light rays directly emitted by source 1 but receives, through a first annular opening 8 in diaphragm 3, a part of the beam of diffused light emitted by an annular-shaped volume of ambient air such as 9 illuminated by source 1 and surrounding it.

Figure 2A:
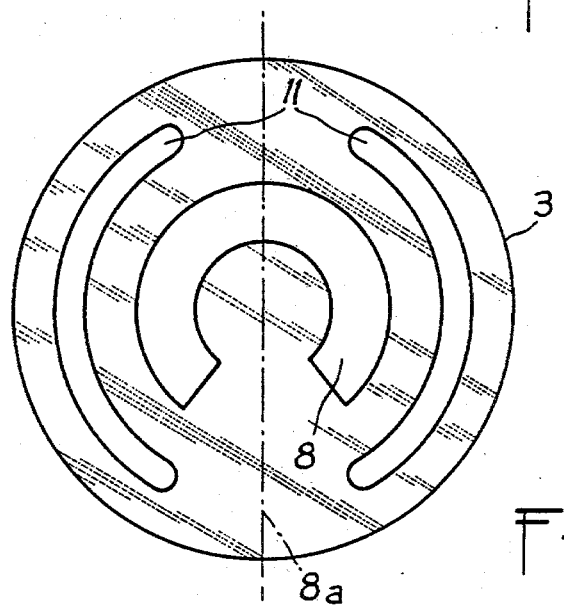
FIG. 2a is a plan view of the diaphragm used in the device represented in FIGS. 1 and 2b.

The second detector 4, the sensitive surface 4a of which is turned in the direction opposite source 1, receives a beam formed from rays such as 10 which are directly emitted by source 1 and reflected along 10a and 10b by concave mirror 5, said rays 10 passing through a second annular opening 11 in diaphragm 3. As seen in FIG. 2a, the second opening 11 is concentric to, and surrounds, the first opening 8 in diaphragm 3. The openings 8 and 11 are coaxial with the optical axis 12 of the apparatus, this axis being constituted by a straight line connecting source 1 with the centers of detectors 2 and 4 and of mirror 5. Axis 12 coincides with the common axis of dark cones 6a and 6b of divergent beam 1a.

The angle of opening "$\alpha$" of beam 1a, measured within the plane containing axis 12, is 126° in the example shown. This angle is advantageously between 50° and 170°. In the example shown, the half-angle at peak "$\theta_1$" of dark cone 6a and the half-angle at peak "$\theta_2$" of dark cone 6b are equal and measure 27°.

Figure 2B:
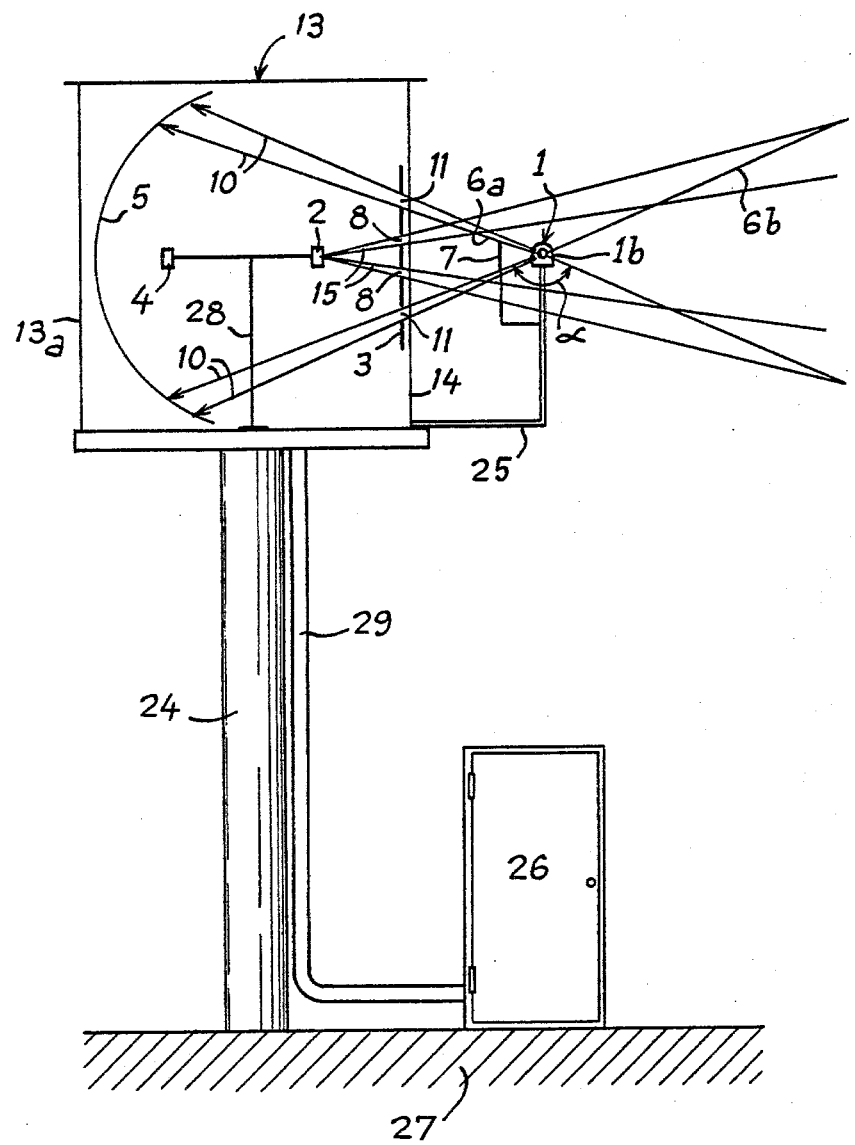
FIG. 2b is a schematic view, elevated and in vertical cross-section, of the installation of a device according to one embodiment of the invention.

Detectors 2 and 4 are thus aligned with source 1 and are coaxial with beam 1a, mirror 5 and diaphragm 3. Detectors 2 and 4, diaphragm 3 and mirror 5 are disposed within a receiver housing 13 of which only surface 14 directed towards source 1 is transparent, e.g. made of glass, in order to let through both beam 15 of light diffused by the volume of air 9 surrounding source 1, and light rays 10 emitted directly by source 1, as shown in FIGS. 1 and 2b.

Figure 3:
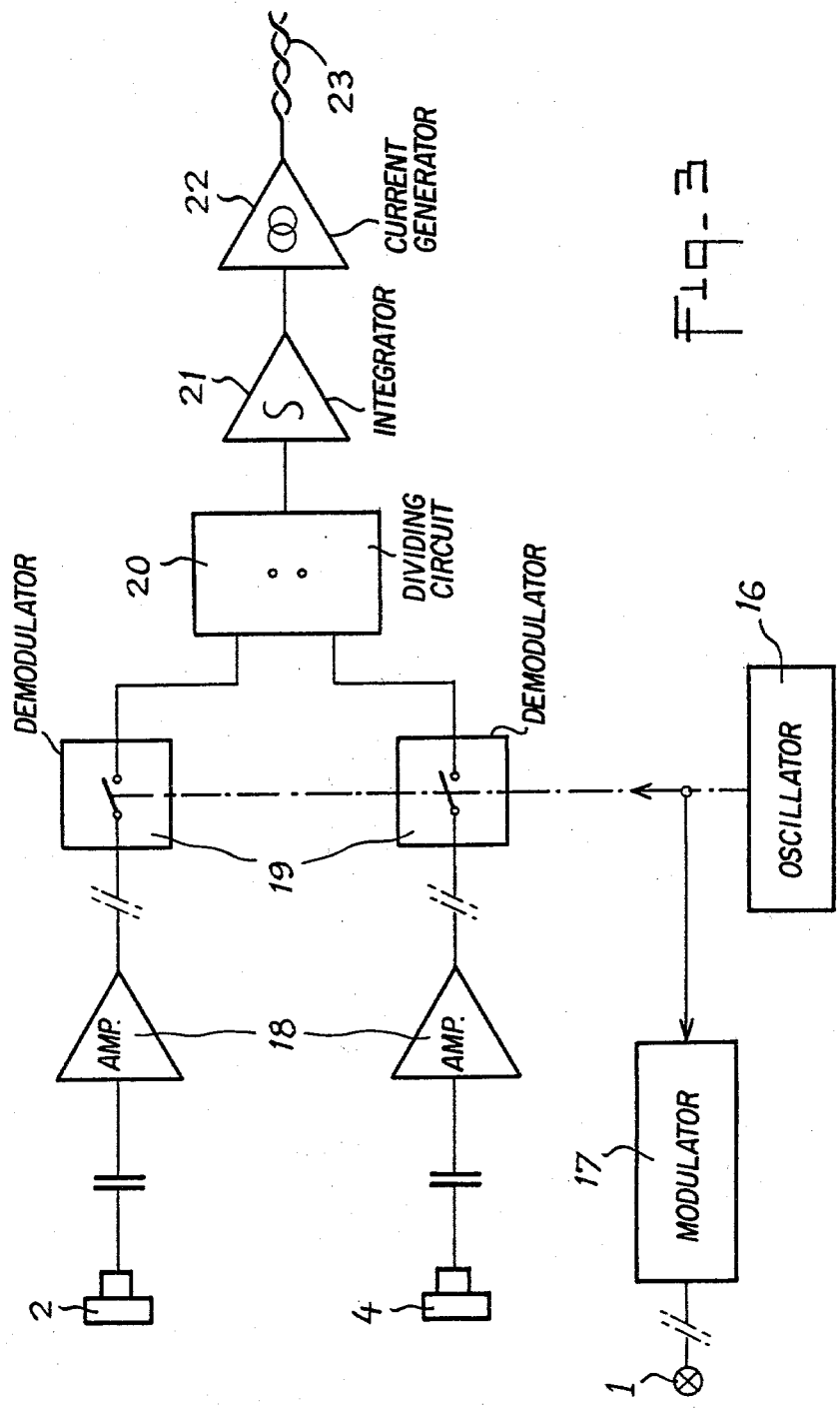
FIG. 3 is an electrical block diagram of the device represented in FIGS. 1 and 2 according to one embodiment of the invention.

As shown in the diagram of FIG. 3, a pilot oscillator 16 controls the modulation of the power current of source 1 by a modulator 17. The modulated signal provided by each detector 2 and 4 is amplified by selective amplifiers 18 then demodulated in the demodulators 19 controlled by pilot oscillator 16.

The demodulated signals are then divided, one by the other, in a dividing circuit 20. The signal provided by the circuit 20 is integrated over a predetermined period, e.g. several minutes, in an integrating circuit 21 and the integrated signal is transformed into a current signal in current generator 22 for feeding to a telephone line 23 transmitting the visibility measurement data to a distant station.

The operating principle of the device just described is explained below in greater detail.

The light source, or lamp, 1 is compact or quasi-pinpoint in shape. This source illuminates the misty ambient air, which may have an aerosol composition, outside the apparatus. There results an emission, by the volume of air 9 defined optically by circular annular opening 8, of the diffused light beam including the diffusion of the incident light within a large angular field. The data delivered by the cell, or detector, 2 illuminated by the diffused beam is proportional to the diffusion coefficient of the misty air in the angular field defined by $\theta_1$ and $\theta_2$. The second cell 4 is illuminated by a portion of direct beam 1a provided by source 1, a portion limited by the second opening 11 in diaphragm 3.

The modulated signal provided by the two cells 2 and 4 is amplified by selective amplifiers 18, eliminating the continuous level due to ambient illumination. After demodulation of the two signals in circuits 19, divider 20 carries out the diffused flow/direct flow ratio.

With the aim of smoothing out pinpoint variations in diffusion, the information provided by divider 20 is integrated over a period of several minutes in integrator 21.

The use of two cells 2 and 4, the illumination of which is proportional respectively to the diffused flow and the direct flow emitted by lamp 1, enables independence from variations in the flow time emitted by lamp 1 (aging), from stains on the surface of glass entry 14, and, in large part, from drifts (due to aging and to variations in outside temperature) of cell 2 and of amplification circuits 18.

In practice, the angular field over which diffusion is observed is limited. In fact, the technical and geometric structure of lamp 1 dictates that it is not a perfectly diffusing source. In addition, the angle of opening 2 $\theta_1$ of dark cone 6a must be sufficient to avoid stray diffusion, especially over opening 8 of the diaphragm which defines the flow received by cell 2.

Under these circumstances, angle "$\alpha$" of beam 1a is advantageously approximately 120°. At this opening, it has been observed that the maximum error in the measurement of the diffusion coefficient is less than 11%.

In addition, analysis air volume 9 cannot be a complete circular ring. In fact, it is desirable to mask stray reflections due to the ground and to the metal structure supporting source 1. Consequently, the radiation diagram of source 1 in the plane perpendicular to axis 12 of the apparatus has, advantageously, an angle of opening of approximately 240°. In FIG. 2a, it can be seen that opening 8 is a portion of a circular ring extending approximately 240°, while opening 11 comprises two circular ring portions each extending approximately 120°, the two portions being disposed symmetrically on either side of the axis of symmetry 8a of opening 8. Diaphragm 3 is disposed within housing 13 in such a way that axis 8a is vertical.

Calibration of the apparatus can be performed with the aid of an annular piece of plastic material having a known diffusion coefficient. This piece covers the entirety of volume 9. The piece is hollowed out at the center so as to permit unattenuated transmission of the direct flow to itself.

According to the embodiment represented in FIG. 2b, the apparatus comprises two distinct assemblies, each having its own function:

- a "captor" assembly mounted on a support pole 24, composed of light transmitter 1 connected rigidly to receiving housing 13 by means of support arm 25; and
- electronic assembly 26, including the power and control circuits 16 and 17 and amplification and transmission circuits 19 through 22. The assembly 26 is disposed at the foot of support 24 in a leaktight case.

Assembly 1, 13 is rotationally symmetrical around an axis 12 which passes through the geometrical centers of receiver 2 through 5, 8, 11 and 13 of transmitter 1, 7. The axis 12 is advantageously disposed horizontally.

The volume of air analyzed 9 is in the shape of an annular ring truncated at the bottom so as to avoid reflections due to the ground 27 and to transmitter support arm 25.

Transmitter 1, affixed at the extremity of arm 25 integral with the receiver, is advantageously constituted by a source of modulated white light aligned upon its support and protected by a glass. Source 1 may either be a filament lamp or a lamp of the electric arc type in a xenon atmosphere. A filament lamp enables obtainment of a satisfactory signal/interference ratio even in the case of great visibility; electric arc lamps offer relatively reduced permanent consumption and a low thermic time constant enabling a high modulation rate.

Angles $\alpha$, $\theta$, and $\theta_2$ are delimited by the source support itself.

Receiver housing 13 consists of a cast aluminum piece to which transmitter support arm 25 is affixed. The housing 13 interlocks with support pole 24. Access to the interior of housing 13 is facilitated by the removable back 13a of the housing 13. The front of housing 13 is closed by a flat optical glass 14 which permits fast and easy cleaning. This arrangement further ensures a practically uniform distribution of any stains on the glass.

The mechanical parts inside cast housing 13 include a support 28 for two photodiodes each constituting a detector 2, 4; and one or several diaphragms, such as 3, 8, 11, limiting the solid angles of direct 10 and diffused 15 light flows.

Connected to each detector 2, 4, a low-noise amplifier 18 ensures adaptation and transmission of the signals between the detector and electronic assembly 26.

The direct flow 10 detected by cell 4 is limited in entering the receiver by the two half moon sections of opening 11. Concentration of the flow 10 on cell 4 is ensured by the geometry and surface state of mirror 5 which constitutes the inner back of housing 13. The shape of diaphragm openings 8, 11 are conceived so as to achieve the greatest possible independence from stains on protective glass 1b of light source 1.

The diffused flow 15 illuminating cell 2 is defined by diaphragm opening 8 shaped so as to mask possible stray reflections due to the ground 27 and to transmitter support arm 25.

The receiver block assembly 13, 14 is thermally insulated and regulated so as to limit temperature drift in cells 2 and 4 and amplifiers 18.

Electrical assembly 26 is in the form of a parallelepiped, leaktight case. It is connected to captor 1, 13 by a cable 29 which conveys the following currents or signals: modulation signal from light source 1; detection signals of direct and diffused flow; and power currents of amplifiers 18 connected to cells 2 and 4.

The electrical assembly is constructed in modular form, thus facilitating repair and maintenance of the equipment.

The advantages of the above-described apparatus and installation are given below.

Separation of the electronics from the captor lightens the latter and thus enables use of a support pole, or mast, 24 of smaller diameter.

In certain applications, such as implantation of the apparatus on a buoy or in an isolated station, the electronics may be integrated within the body of the measurement unit.

Since the capacity of the case holding assembly 26 is not limited a priori, the modular conception enables possible adaptation to various visibility data transmission systems, output current module or radiotransmitter modulator module, etc.

It is not claimed that the apparatus according to the invention may serve as a substitute, in aeronautic applications in particular, for a classic transmittometer, of which the precision for visibilities of less than a few kilometers has proven far greater. However, for the applications intended, the apparatus offers sufficient precision as well as notable advantages, especially: very reduced infrastructure; installation and start-up requiring only several minutes (no alignment problems); good protection against glass stains due to the compensation loop; reduced electrical power consumption; light weight enabling rapid maintenance by complete replacement of the captor; and low cost of manufacture.

In contrast to known devices of like principle, the present apparatus offers the following particularities and advantages: analysis air volume of annular shape offering large volume; large angle of opening of the light source ensuring good precision in measurement of the total diffusion coefficient; absence of photomultiplier thanks to use of cells having great sensitivity and excellent linearity; limitation of stray reflections off of ground and metal support by special configuration of diaphragm openings; and automatic compensation loop for stains which takes their possible nonuniformity into account.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A device for measuring the visibility or diffusion coefficient of atmospheric ambient air, comprising:
   a light source for emitting a direct light beam on a predetermined volume of said ambient air, said light beam diverging in a predetermined solid angle and defining at least one dark cone, outside of said solid angle, in which no direct light beam from said source is directed;
   a receiver including at least a first detector which defines an optical axis with the light source, said first detector located in the dark cone and having at least a first entry window also within said dark cone;
   wherein the solid angle of the direct light beam extends angularly on substantially both sides of a plane perpendicular to the optical axis and proceeding from the center of said source, such that said first detector receives through said first entry window the light diffused by said volume of air along angles of diffusion distributed within a wide diffusion field which may spread from several degrees up to 170°;
   means for averaging the diffused light detected by said receiver so as to counter the influence of the nature of the aerosol on the quantity measured;
   said receiver further including a second detector intended to measure the flow of light by said source, said second detector receiving directly a portion of the beam emitted by said source; and a second entry window for said second detector, said second entry window having an essentially annular shape and surrounding said first entry window.

2. A visibility measuring device according to claim 1, further comprising:

the diffusion filed defined by the solid angle of the direct light beam lying within a range of from 50° to 170°.

3. A visibility measuring device according to claim 1, further comprising:

said direct light beam and said first detector entry window are each in appreciably rotational form centered on the optical axis, in consideration of which said examined volume of air is increased so that said first entry window may be of small surface so as to avoid reception of stray light by said first detector without notably reducing the quantity of diffused light received by said first detector.

4. A visibility measuring device according to claim 1 or 3, further comprising:

the diffusion field defined by the solid angle of the direct light beam extending at least 25° from each side of said plane perpendicular to the optical axis.

5. A visibility measuring device according to claim 3, further comprising:

said first detector entry window having an essentially annular shape.

6. A visibility measuring device according to claim 4, further comprising:

said first detector entry window having an essentially annular shape.

7. A visibility measuring device according to claim 1, 3 or 5, further comprising:

the diffusion field defined by the solid angle of the direct light beam extending angularly with respect to the optical axis in the direction of the detector from a minimum angle of between 5° and 40°.

8. A visibility measuring device according to claim 4, further comprising:

the diffusion field defined by the solid angle of the direct light beam extending angularly with respect to the optical axis in the direction of the detector from a minimum angle of between 5° and 40°.

9. A visibility measuring device according to claim 1, further comprising:

said first and second entry windows formed by the respective openings in a single diaphragm.

10. A visibility measuring device according to claim 1, further comprising:

a closed, thermally insulated enclosure having a transparent surface facing the source, said first and second detectors disposed in said enclosure.

* * * * *